US009265944B2

United States Patent
Sürth et al.

(10) Patent No.: US 9,265,944 B2
(45) Date of Patent: Feb. 23, 2016

(54) TRIPHASIC PULSES TO REDUCE UNDESIRABLE SIDE-EFFECTS IN COCHLEAR IMPLANTS

(71) Applicant: MED-EL Elektromedizinische Geraete GmbH, Innsbruck (AT)

(72) Inventors: Werner Sürth, Axams (AT); Reinhold Schatzer, Birgitz (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 14/334,743

(22) Filed: Jul. 18, 2014

(65) Prior Publication Data

US 2015/0025597 A1   Jan. 22, 2015

Related U.S. Application Data

(60) Provisional application No. 61/856,090, filed on Jul. 19, 2013.

(51) Int. Cl.
*A61N 1/36* (2006.01)

(52) U.S. Cl.
CPC .................................. *A61N 1/36032* (2013.01)

(58) Field of Classification Search
CPC ................................................ A61N 1/36032
See application file for complete search history.

(56) References Cited

U.S. PATENT DOCUMENTS

2007/0225767 A1* 9/2007 Daly et al. .................. 607/2
2012/0130449 A1   5/2012 Carlyon et al. ............. 607/57
2012/0191161 A1   7/2012 van Dijk .................... 607/57

OTHER PUBLICATIONS

International Searching Authority, International Search Report and Written Opinion—PCT/US2014/047123 date of mailing Dec. 5, 2014, 16 pages.
MED EL Medical Electronics, "Sonata Ti$^{100}$Cochlear Implant Manual (online)", Med-El, Jan. 24, 2013, [retrieved on Oct. 28, 2014 from the internet—http:www.medel.com/data/pdf20332E.pdf entire document, 20 pages.

* cited by examiner

*Primary Examiner* — George Evanisko
(74) *Attorney, Agent, or Firm* — Sunstein Kann Murphy & Timbers LLP

(57) ABSTRACT

An arrangement for operating a cochlear implant system is described. Stimulation signals are applied to stimulation electrodes in a cochlear implant electrode with an initial signal format using biphasic electrical stimulation pulses. One or more undesired somatic responses to the stimulation pulses are identified. The one or more undesired somatic responses are reduced by selecting an adapted signal format using charge-balanced triphasic electrical stimulation pulses to apply stimulation signals to one or more of the stimulation electrodes.

8 Claims, 4 Drawing Sheets

TRIPHASIC PULSES TO REDUCE UNDESIRABLE SIDE-EFFECTS IN COCHLEAR IMPLANTS

This application claims priority from U.S. Provisional Patent Application 61/856,090, filed Jul. 19, 2013, which is incorporated herein by reference in its entirety.

FIELD OF THE INVENTION

The present invention relates to coding stimulation pulses for cochlear implant systems, and specifically to such pulse coding so as to reduce undesired somatic effects in the implanted patient.

BACKGROUND ART

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode contact can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Along the elongate axis of the electrode array 110 on its surface are multiple electrode contacts 112 that provide selective stimulation of the cochlea 104.

The standard stimulation pulses in cochlear implants are biphasic. As shown in FIG. 2, such biphasic stimulation pulses have a negative half-wave (cathodic phase) and a charge-balanced positive half-wave (anodic phase). The net charge of a given half-wave pulse corresponds to the product of its current amplitude A and its pulse duration T. To ensure that no DC components are transmitted to the auditory nerve, the biphasic stimulation pulse includes an opposite phase half-wave pulse of equal duration and opposite amplitude to the first half-wave pulse. In specific pulsatile stimulation strategies, sequential or parallel pulses can be generated at different stimulation electrodes.

Sometimes, depending on the propagation of the electrical stimulation field and the specific anatomical situation, other nerves may be stimulated inadvertently. Such collateral stimulation can result in unintended side-effects such as twitching of the eye or a burning sensation in the tongue or in the throat. These unpleasant side-effects increase in intensity with increasing charge. In some cases, this situation can prevent setting the stimulation intensity sufficiently high for effective hearing via the cochlear implant. If only one or a few stimulation electrodes are affected, these stimulation electrodes can be deactivated. But this change in the operation of the cochlear implant may have other undesirable consequences for the patient. If a considerable number of or all of the stimulation electrodes are affected, the cochlear implant may not be usable for hearing in extreme cases.

When setting the stimulation parameters in a patient fitting process, the fitting audiologist can try to change various stimulation parameters such as pulse width, stimulation rate and compression to provide a louder auditory sensation and reduce the side-effects. Re-implantation with a cochlear implant with a differently arranged reference electrode also has been attempted by placing separate ground electrodes at very specific locations. EP 0959 943 mentions that facial nerve stimulation is an unwanted somatic effect. US 2012/0143284 also discusses the problem of undesirable facial nerve stimulation and other unwanted side-effects. But throughout these documents this issue is always discussed in connection with extra-cochlear electrodes which are considered the source of these effects.

U.S. Pat. No. 5,601,617 describes selecting complex stimulus waveforms including triphasic pulses based on the "response" of the stimulated tissue. Generally the discussion assumes that this is the perceptive response and there is no mention of mitigating adverse stimulus effects.

SUMMARY OF THE INVENTION

Embodiments of the present invention are directed to an arrangement for operating a cochlear implant system. Stimulation signals are applied to stimulation electrodes in a cochlear implant electrode with an initial signal format using biphasic electrical stimulation pulses. One or more undesired somatic responses to the stimulation pulses are identified. The one or more undesired somatic responses are reduced by selecting an adapted signal format using charge-balanced triphasic electrical stimulation pulses to apply stimulation signals to one or more of the stimulation electrodes.

A variation of the adapted signal format includes charge-balanced triphasic electrical stimulation pulses whereby gaps are introduced between the first and second, and between the second and third pulse phases. These gaps are designated as inter-phase-gaps and can range from 0 to several hundred microseconds, i.e. they are on the same order of magnitude than the individual pulse phase durations. The inter-phase gaps may be symmetric (equal duration) or asymmetric (unequal duration). Yet another variation of the adapted signal format includes charge-balanced biphasic electrical stimulation pulses with one inter-phase gap between the first and second pulse phase. The duration of this inter-phase gap is on the same order of magnitude than the pulse phase durations.

The triphasic electrical stimulation pulses may include first and third phase pulses matching each other in phase and opposite in phase to a second phase pulse. An alternative electrical stimulation pulse for avoiding undesired somatic responses may be a biphasic stimulation pulse with a gap between the first and second pulse phase. The gap duration is on the order of magnitude of the pulse phase duration. All the phase pulses are equal in amplitude or duration. The first phase pulse may be anodic or cathodic. The triphasic electrical stimulation pulses may be formed from consecutive biphasic pulses of opposite polarity. The adapted signal format may apply the stimulation pulses to the one or more stimulation electrodes sequentially one stimulation electrode at a time, or in parallel to multiple stimulation electrodes at a time.

DETAILED DESCRIPTION OF SPECIFIC EMBODIMENTS

Figure 1:
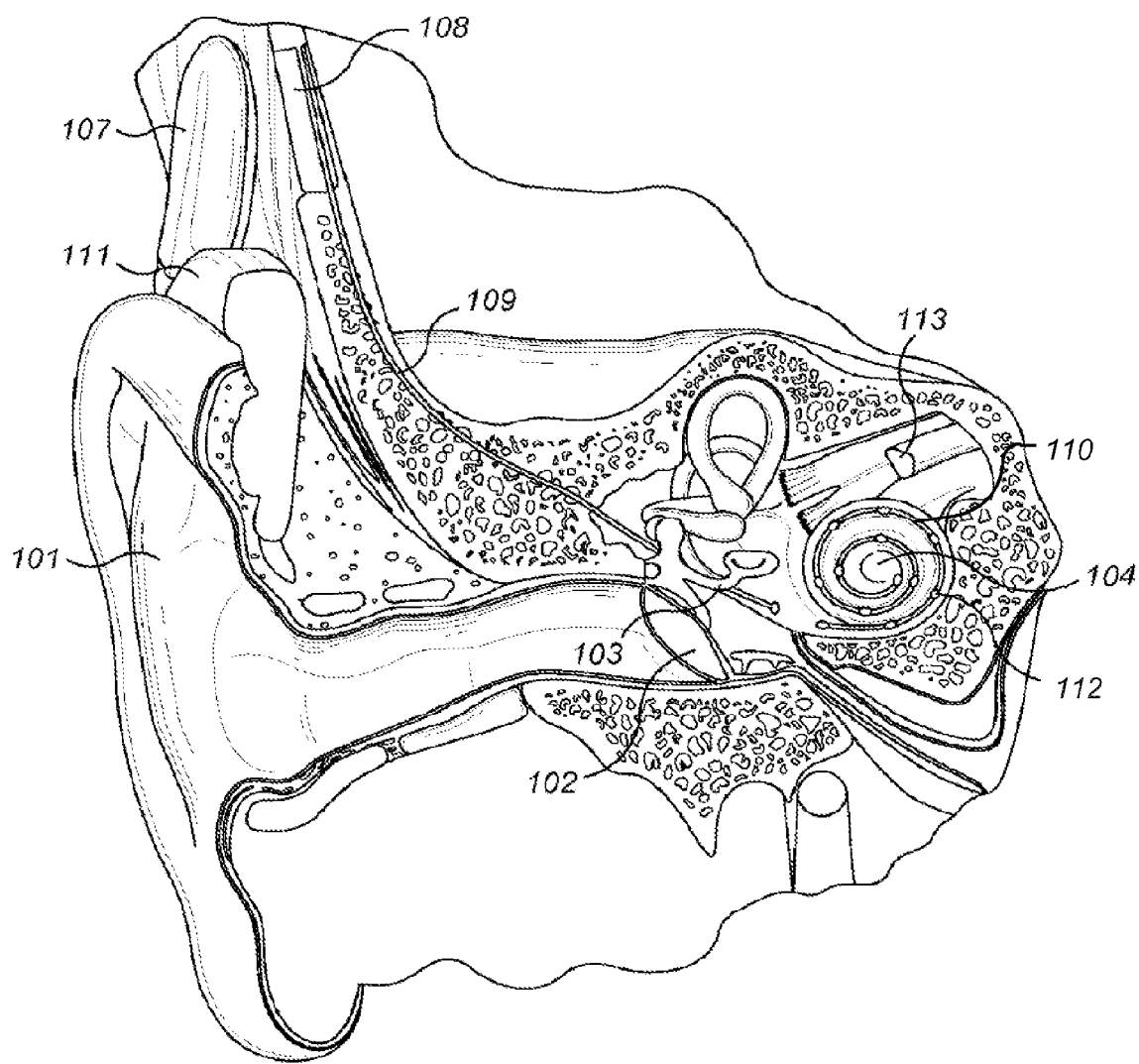
FIG. 1 shows anatomical structures in a human ear having a cochlear implant system.
Figure 2:
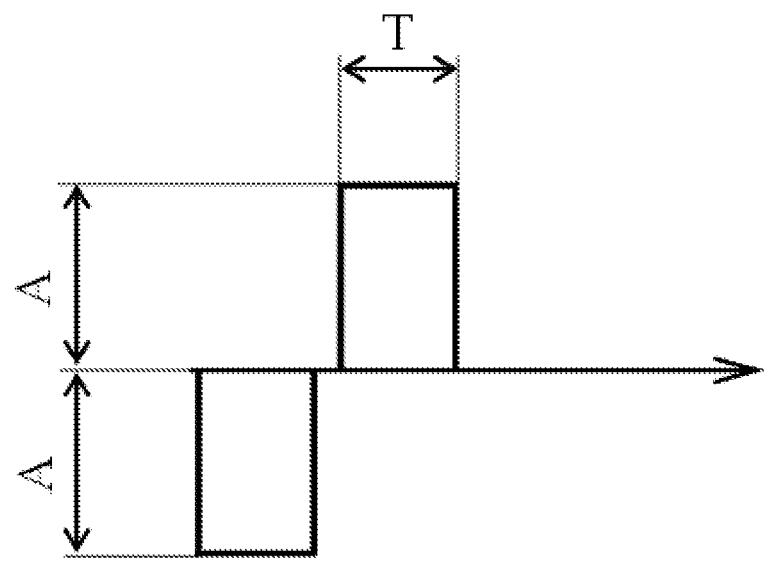
FIG. 2 shows an example waveform for a typical biphasic stimulation pulse.

In addition to the typical biphasic stimulation pulses, most modern cochlear implants are capable of generating symmetrical triphasic pulses. But biphasic rather than triphasic pulses conventionally are used for cochlear implant stimulation in a normal operation mode (i.e. when the patient's auditory nerve is stimulated in order to provide auditory sensation. The situation is different for the non-hearing situation of measuring nerve responses to stimulation pulses where it is known that triphasic stimulation pulses may favourably reduce stimulation artifacts). No one in the field has identified any particular advantage to using triphasic stimulation pulses rather than biphasic stimulation pulses—biphasic stimulation pulses work just fine so there has been no perceived need for using triphasic pulses. In addition, if the individual pulses phases (positive and negative) become too short (e.g. shorter than about 10 µs), then a triphasic stimulation pulse that splits the duration of one of the pulse phases may lead to an uncertain charge balance because of the limited temporal resolution of the stimulation system. That issue is not any sort of fundamental limit but rather is a purely technical one. Still there was no reason to put any significant effort into reliable higher temporal resolution that could use much shorter pulse phases with a duration of just 2 or 3 µs while still reliably ensuring charge balance between the positive and negative pulses phases. Moreover, the overall maximum stimulation rate could be considerably decreased when using triphasic pulses.

So the potential use of triphasic stimulation pulses for cochlear implant systems has been mentioned before. And the problem of adverse side effects such as facial nerve stimulation has long been known. But no one in the field has ever suggested that triphasic stimulation pulses might be used to prevent or mitigate such adverse effects. And Applicant has determined that, in contrast to conventional biphasic pulses, triphasic pulses can significantly reduce unwanted side-effects while providing the desired loudness perception to the patient.

Embodiments of the present invention are directed to an arrangement for operating a cochlear implant system based on using triphasic stimulation pulses to avoid undesired somatic effects. Initially stimulation signals are applied to stimulation electrodes in a cochlear implant electrode with an initial signal format using conventional biphasic electrical stimulation pulses. When one or more undesired somatic responses to the stimulation pulses are identified, those are reduced by selecting an adapted signal format using charge-balanced triphasic electrical stimulation pulses to apply stimulation signals to one or more of the stimulation electrodes.

The adapted signal format may apply the stimulation pulses to the one or more stimulation electrodes sequentially one stimulation electrode at a time, or in parallel to multiple stimulation electrodes at a time. The triphasic pulses may be applied to individual stimulation electrodes, to one or more sub-groups of stimulation electrodes, or to all the stimulation electrodes. They may be applied sequentially at different electrodes or in parallel.

Figure 3:
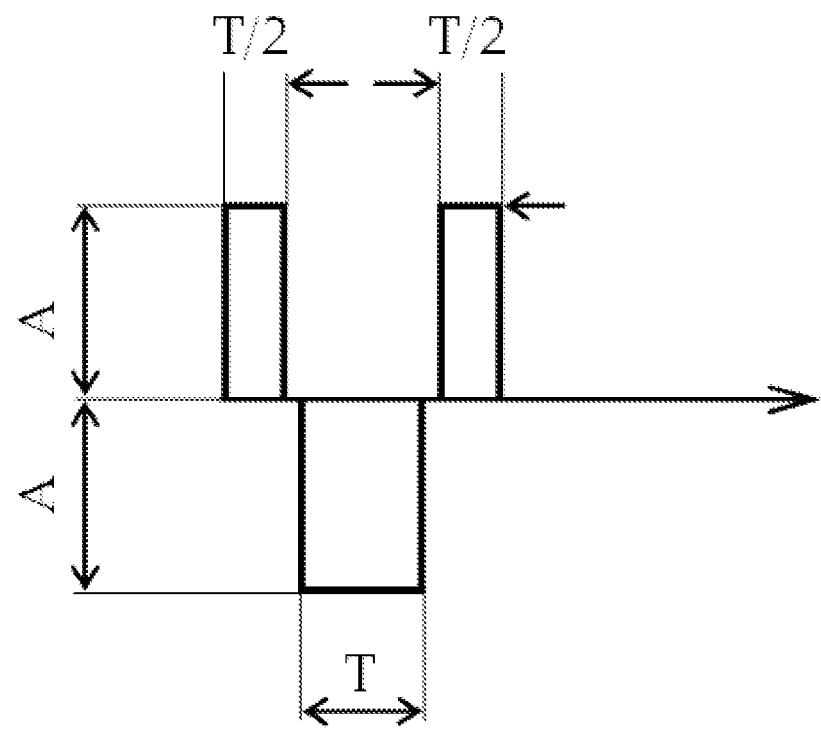
FIG. 3 shows an example waveform for one specific type of triphasic stimulation pulse according to an embodiment of the present invention where all the pulse phases have equal amplitudes and the first and third pulse phases are each half the duration of the second pulse phase.

FIG. 3 shows an example waveform for one specific type of triphasic stimulation pulse according to an embodiment of the present invention where first and third phase pulses match each other in phase and are opposite in phase to a second phase pulse. In the waveform shown in FIG. 3, all the pulses phases have equal amplitude values with the first and third pulse phases each being half the duration of the opposite second pulse phase. In the waveform shown in FIG. 3, the first and third phase pulses are anodic (positive) and the second phase pulse is cathodic (negative). In other embodiments, it may be the reverse case.

Figure 4:
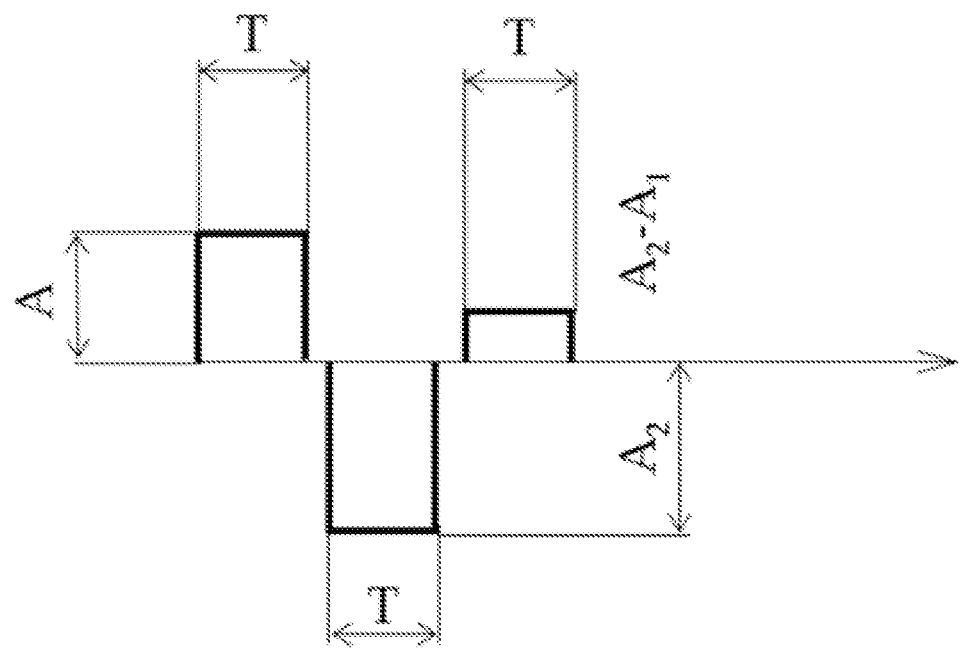
FIG. 4 shows an example waveform for another specific type of triphasic stimulation pulse according to another embodiment of the present invention where all the pulse phases have equal durations and the combined amplitudes of the first and third pulse phases are equal and opposite to the amplitude of the second pulse phase.

FIG. 4 shows an example waveform for another specific type of triphasic stimulation pulse according to another embodiment of the present invention using what are referred to as precision pulses. By that it is meant that all the pulse phases have equal durations and different amplitude values where the combined amplitudes of the first and third pulse phases are equal and opposite to the amplitude of the second pulse phase.

Figure 5:
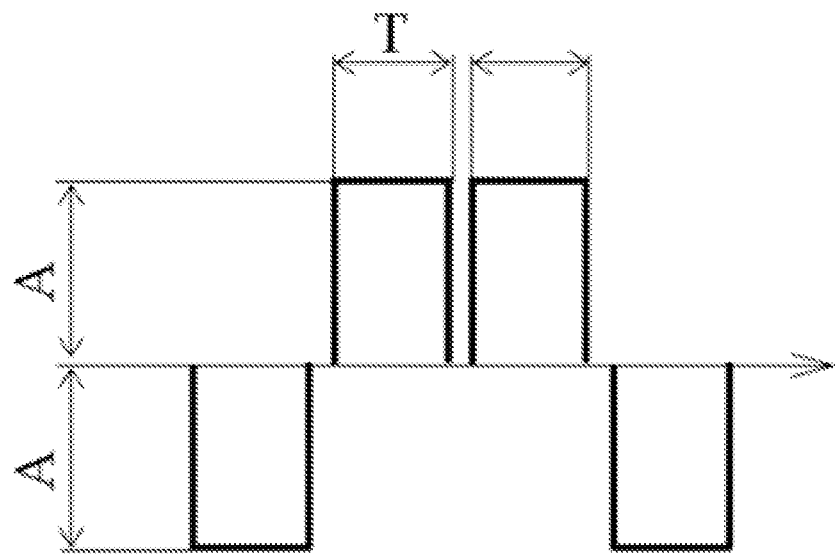
FIG. 5 shows an example waveform for another specific type of triphasic stimulation pulse according to another embodiment of the present invention based on back-to-back biphasic pulses of opposite phase.

FIG. 5 shows an example waveform for another specific type of triphasic stimulation pulse according to another embodiment of the present invention for systems which may not be capable of forming symmetrical triphasic stimulation pulses. In that case, triphasic pulses can be formed as shown based on back-to-back biphasic pulses of opposite phase.

Figure 6:
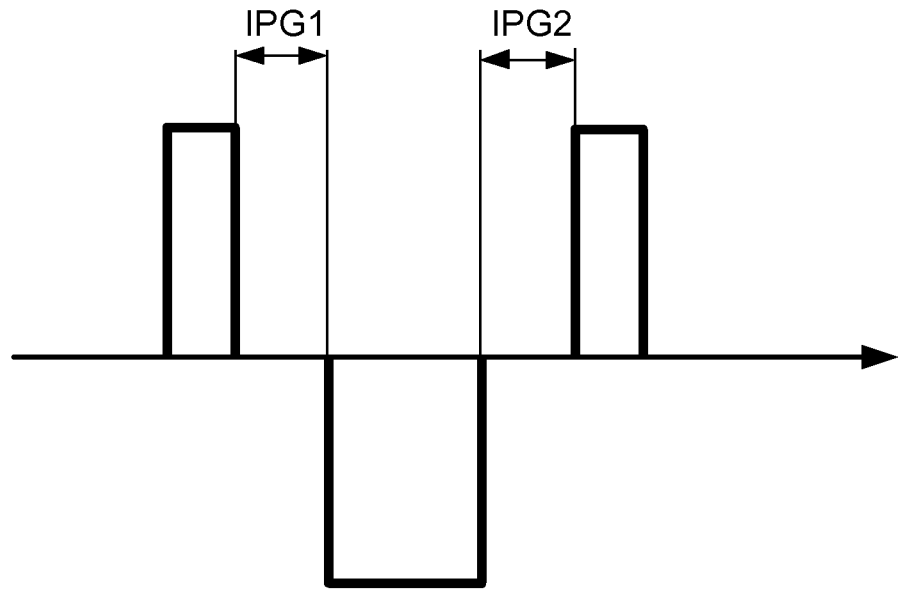
FIG. 6 shows an example waveform for another specific type of triphasic stimulation pulse according to another embodiment of the present invention based on inter-phase gaps between the first and second and between the second and third pulse phases.
Figure 7:
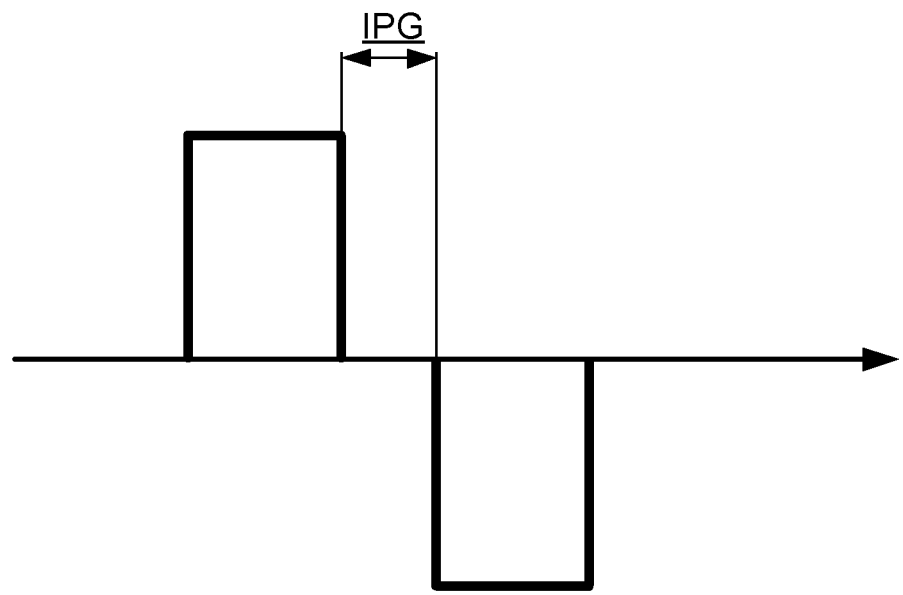
FIG. 7 shows an example waveform for another type of biphasic stimulation pulse according to another embodiment of the present invention based on an inter-phase gap between the first and second pulse phases.

FIG. 6 shows an example waveform for another specific type of triphasic stimulation pulse according to another embodiment of the present invention wherein the adapted signal format includes inter-phase gap periods between adjacent phase pulses; i.e., between the first and second ("IPG1"), and/or between the second and third pulse phases ("IPG2"). These inter-phase gaps IPG1 and IPG2 are on the same order of magnitude as the individual pulse phase durations, and so typically can range from zero to several hundred microseconds. In some specific embodiments, the inter-phase gaps may be variable in duration to adjust the one or more undesired somatic responses, and/or the inter-phase gaps may be symmetric (equal duration) or asymmetric (unequal duration). FIG. 7 shows an example waveform for another embodiment of the present invention based on a biphasic stimulation pulse with an inter-phase gap between the first and second pulse phases.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of operating a cochlear implant comprising:
    applying stimulation signals with an initial signal format using biphasic electrical stimulation pulses to stimulation electrodes in a cochlear implant electrode;
    identifying an undesirable facial nerve stimulation response to the stimulation pulses; and
    selecting an adapted signal format that reduces the undesirable facial nerve stimulation response by using charge-balanced triphasic electrical stimulation pulses to apply stimulation signals to one or more of the stimulation electrodes.

2. A method according to claim 1, wherein the triphasic electrical stimulation pulses include first and third phase pulses matching each other in phase and opposite in phase to a second phase pulse.

3. A method according to claim 2, wherein all the phase pulses are equal in amplitude.

4. A method according to claim 2, wherein all the phase pulses are equal in duration.

5. A method according to claim 2, wherein the adapted signal format includes one or more inter-phase gap periods between adjacent phase pulses.

6. A method according to claim 5, wherein the one or more inter-phase gap periods are variable in duration to reduce the undesirable facial nerve stimulation response.

7. A method according to claim 1, wherein the adapted signal format applies the stimulation pulses to the one or more stimulation electrodes sequentially one stimulation electrode at a time.

8. A method according to claim 1, wherein the adapted signal format applies the stimulation pulses to the one or more stimulation electrodes in parallel to multiple stimulation electrodes at a time.

* * * * *